(12) United States Patent
Boudreaux (10) Patent No.: US 6,461,569 B1
(45) Date of Patent: Oct. 8, 2002

(54) METHOD AND APPARATUS FOR ULTRAVIOLET RADIATION CATHETER STERILIZATION SYSTEM

(75) Inventor: Chad P. Boudreaux, Cincinnati, OH (US)

(73) Assignee: Ethicon Endo Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/714,628

(22) Filed: Nov. 15, 2000

(51) Int. Cl.[7] .............................. A61L 2/00; A61B 1/00; A61M 37/00; A61M 25/00
(52) U.S. Cl. .................. 422/24; 422/292; 600/101; 604/95.01; 604/164.13; 604/167.06; 604/264; 604/510; 604/523
(58) Field of Search .................... 422/22, 24, 292; 600/101; 604/5.8, 510, 95.01, 264, 95.04, 256, 95.05, 523, 164.13, 533, 165.01, 537, 167.02, 167.06

(56) References Cited

U.S. PATENT DOCUMENTS

| 4,736,733 A | * | 4/1988 | Adair |
| 4,762,120 A | * | 8/1988 | Hussein |
| 4,782,819 A | * | 11/1988 | Adair |
| 5,222,949 A | * | 6/1993 | Kaldany |
| 5,260,020 A | | 11/1993 | Wilk et al. |
| 5,334,171 A | * | 8/1994 | Kaldany |
| 5,695,482 A | | 12/1997 | Kaldany |

* cited by examiner

Primary Examiner—Terrance R. Hill
Assistant Examiner—Monzer R. Chorbaji
(74) Attorney, Agent, or Firm—Blakely, Sokoloff, Taylor & Zafman LLP (57) ABSTRACT

Methods and apparatuses for sterlizng a catheter. In one exemplary embodiment, the apparatus comprises a UV radiation source, a catheter having a lumen which is surrounded by the catheter's wall, and a fiber optic cable that is coupled to a UV radiation source. The fiber optic cable is disposed within the catheter's lumen and is capable of emitting UV radiation through the fiber optic cable's wall. In another exemplary embodiment, the apparatus described above further comprises an insertion tube having two separate paths, one path for a fluid source, and one path for a fiber optic cable. The fiber optic cable in one embodiment can easily be inserted when sterilization is needed and simply removed when completed without modification to existing catheter connections and components.

20 Claims, 12 Drawing Sheets

FIG. 7

# METHOD AND APPARATUS FOR ULTRAVIOLET RADIATION CATHETER STERILIZATION SYSTEM

BACKGROUND OF THE INVENTION

The invention relates to methods and apparatuses for effectively sterilizing catheters.

Bacterial infection is a common problem stemming from long-term catheter use. The infection can start around the entry where a catheter is inserted or in the interior of a catheter. Bacterial infection poses serious clinical problems, sometimes leading to death.

To prevent this situation, it is desirable to sterilize the areas of infection, for instance, the point of entry and the interior of a catheter. One common method of sterilization is exposing bacteria to UV radiation. Previous methods of sterilizing a catheter involve incorporating a fiber optic cable, acting as a sterilization device, into the wall of the catheter to be sterilized.

While effective, these methods require an incorporation of a sterilization device into a catheter's interior wall, which is difficult and will require permanent mounting of the device into the catheter. For instance, a catheter will need to be manufactured to include a fiber optic cable within the wall of the catheter before it is used. Thus, a fiber optic cable is permanently mounted within the wall of a catheter whether sterilization is necessary or not. See, for example, U.S. Pat. Nos. 5,260,020 and 5,695,482. The incorporation of a sterilization device into the wall of a catheter is thus costly and complex.

Another problem of the previous methods is that contamination can be introduced into the patient or the sample because a fiber optic cable would share the same path with fluids being injected into a patient or samples being extracted from a patient through a catheter use.

SUMMARY OF THE INVENTION

The present invention provides apparatuses and methods for effectively sterilizing a catheter and the point of entry of a catheter.

In one exemplary embodiment, an apparatus of the present invention includes a UV radiation source, a catheter having a lumen which is surrounded by the catheter's wall, and a fiber optic cable that is coupled to that UV radiation source. The fiber optic cable is freely disposed within the catheter's lumen and is capable of emitting UV radiation through the wall of a fiber optic cable and optionally, through the end of the fiber optic cable.

In another exemplary embodiment, an apparatus according to the present invention further includes an insertion tube having two separate paths, one path for a fluid source, and one path for a fiber optic cable. This insertion tube is connected to a catheter that needs sterilization. A fiber optic cable is inserted in a separate path from the path for fluid source. The fiber optic cable can be inserted when sterilization is needed and optionally, removed when completed without modification to existing catheter connections and components.

An exemplary method according to the present invention includes inserting a fiber optic cable through a lumen of a catheter, transmitting UV radiation through a fiber optic cable to effectively sterilize the infection area, and removing the fiber optic cable when sterilization is completed.

In another exemplary method, a fiber optic cable transmitting UV radiation is introduced into the catheter through one dedicated path of an insertion tube that has two separate paths. An intravenous fluid is introduced into the catheter through the remaining path of the two-path insertion tube.

The above features and advantages of the present invention will be apparent from the following detailed description of preferred embodiments. The drawings are not necessarily drawn to scale but the emphasis is being placed upon illustrating the principles of the present invention.

BRIEF DESCRIPTION OF THE DRAWINGS

FIG. 1A-1 illustrates an enlarged view of a fiber optic cable inserted inside a catheter's lumen according to one exemplary embodiment.

FIG. 1A-2 illustrates another enlarged view of a fiber optic cable inserted inside a catheter's lumen according to one exemplary embodiment.

FIG. 2 illustrates an example of a polished fiber optic cable.

FIGS. 3A-1–4 illustrate examples of configurations of a two-path insertion tube.

FIGS. 5-1–3 illustrate the mechanics of inserting a fiber optic cable into a catheter according to one exemplary embodiment.

DETAILED DESCRIPTION OF THE INVENTION

The reference characters refer to the same parts throughout different views of the invention unless indicated otherwise.

Figure 1:
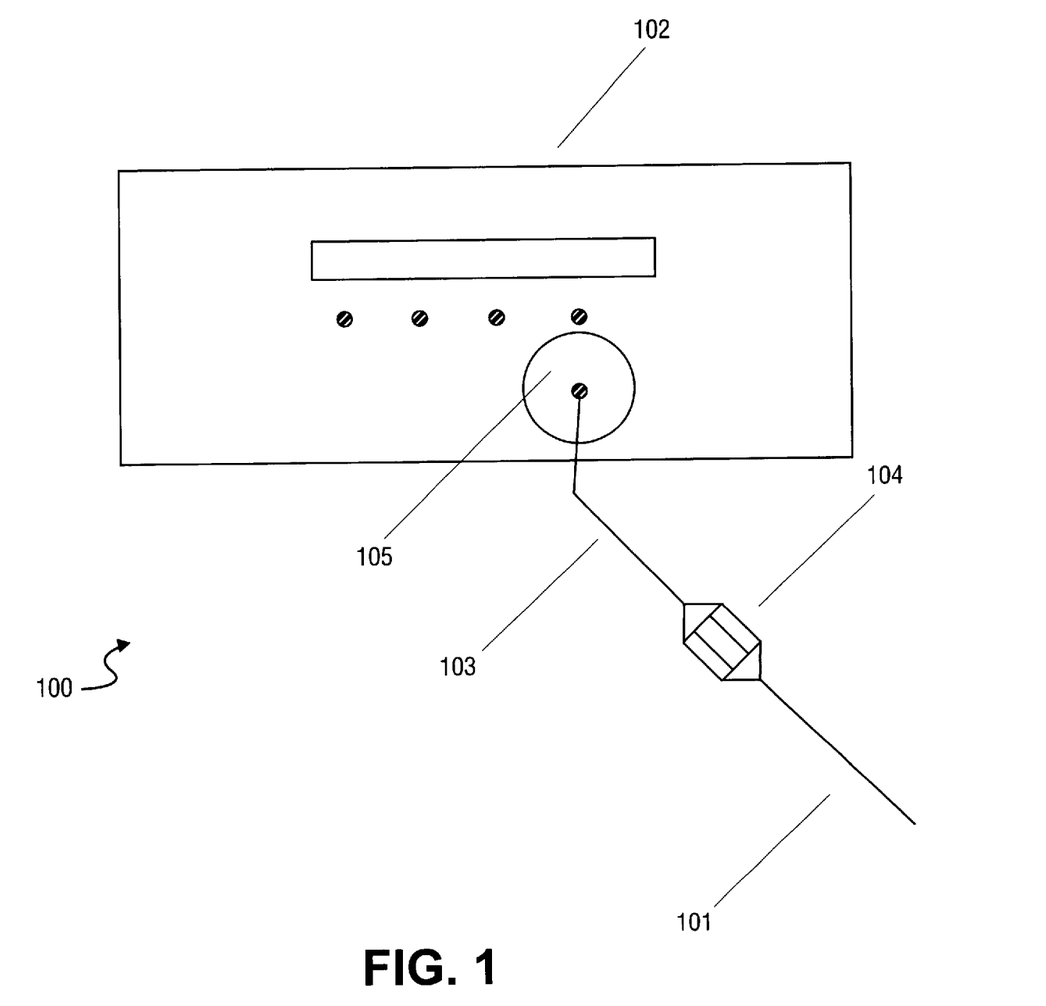
FIG. 1 illustrates an ultraviolet radiation catheter sterilization system according to one exemplary embodiment.

FIG. 1 illustrates, according to one embodiment, components of an ultraviolet (hereinafter UV) radiation catheter sterilization system 100, which comprises catheter 101, UV radiation source 102, and fiber optic cable 103.

Figure 1A:
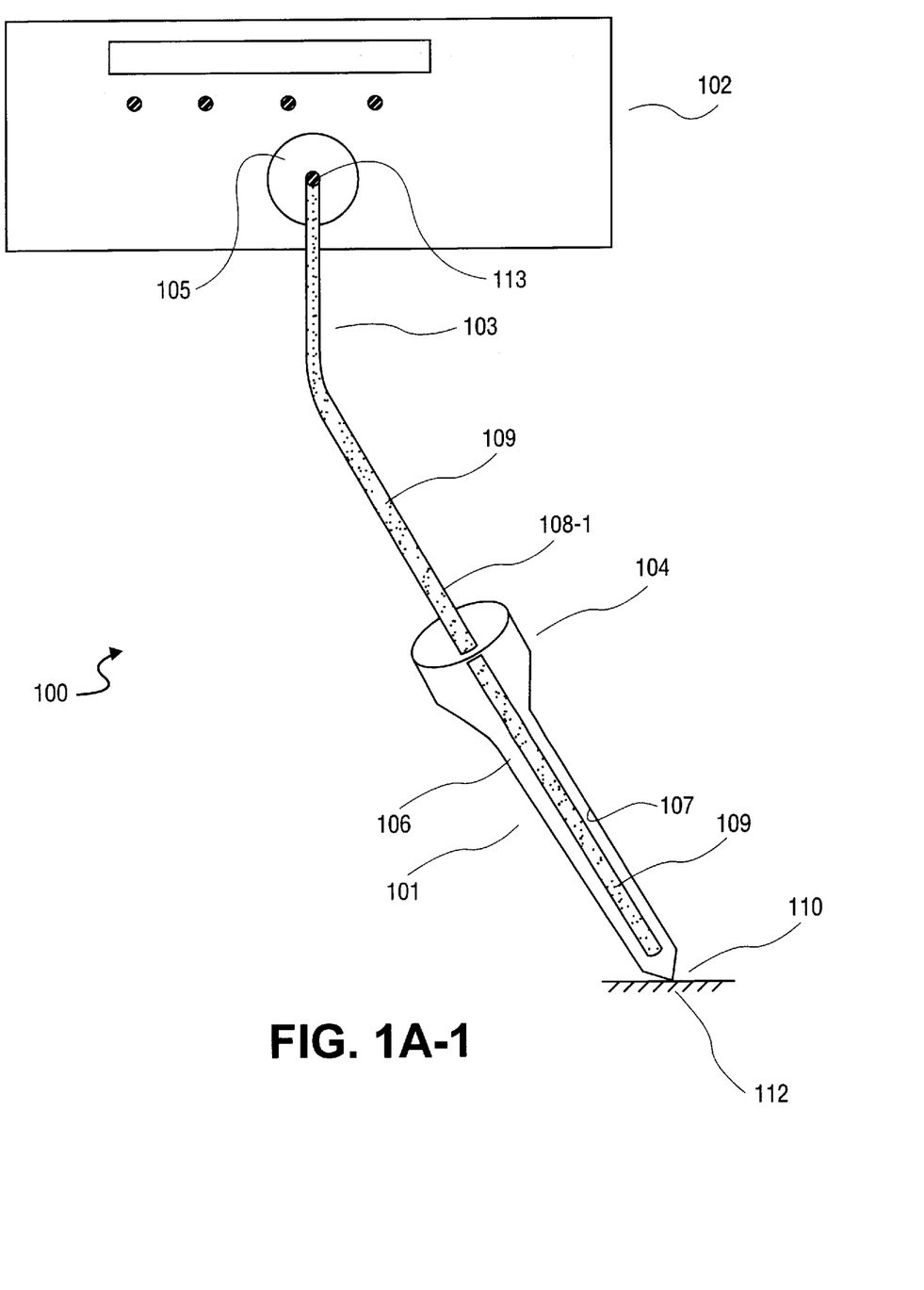

Catheter 101 can be a conventional catheter, readily and commercially available, and preferably a medical grade catheter. FIG. 1A-1 illustrates that catheter 101 has lumen 106 surrounded by internal catheter wall 107. Catheter 101 is typically used for injecting fluid into veins, arteries or tissues from a patient either for a short duration of time or for a long-term duration. Catheter 101 is also sometimes used for extracting fluid or other samples from a patient. Catheter 101 can be made out of a biocompatible plastic polymer, for example, silicon rubber, polypropylene or polyurethane, or stainless steel or metal suitable for use with UV radiation.

As illustrated in FIG. 1A-1, UV source 102 can be a standard UV device, such as a UV lamp, capable of emitting UV radiation for a certain time, duration and power level. UV device 102 may be fitted to accept fiber optic cable 103 using a security attachment 105 such as a bolt, lock or fastener. FIG. 1A-1 also illustrates an enlarged view of fiber optic cable 103 being disposed within catheter's lumen 106. Fiber optic cable 103 can be a UV graded and pure silica based fiber optical cable. Fiber optic cable 103 also comprises fixture 113 at one end of the cable 103 allowing it to be connected to UV radiation source 102.

In one embodiment, catheter 101 can also be made out of UV transparent plastic, such as cellophane or plastics used to make a UV-transparent cuvette for UV spectrophotometer technology. When such a catheter is used, the UV radiation can possibly be emitted outward beyond a catheter tip 110, for example, through catheter's wall 107, thus, UV radiation can reach a broader infection area surrounding the catheter in a patient's body.

FIG. 1A-1 also illustrates one embodiment in which fiber optic cable 103 includes optical fiber 109, which is surrounded by wall 108-1. Fiber optic cable 103 has a dimension defined by wall 108-1, which is less than the dimension of lumen 106 of catheter 101.

Figure 1A:
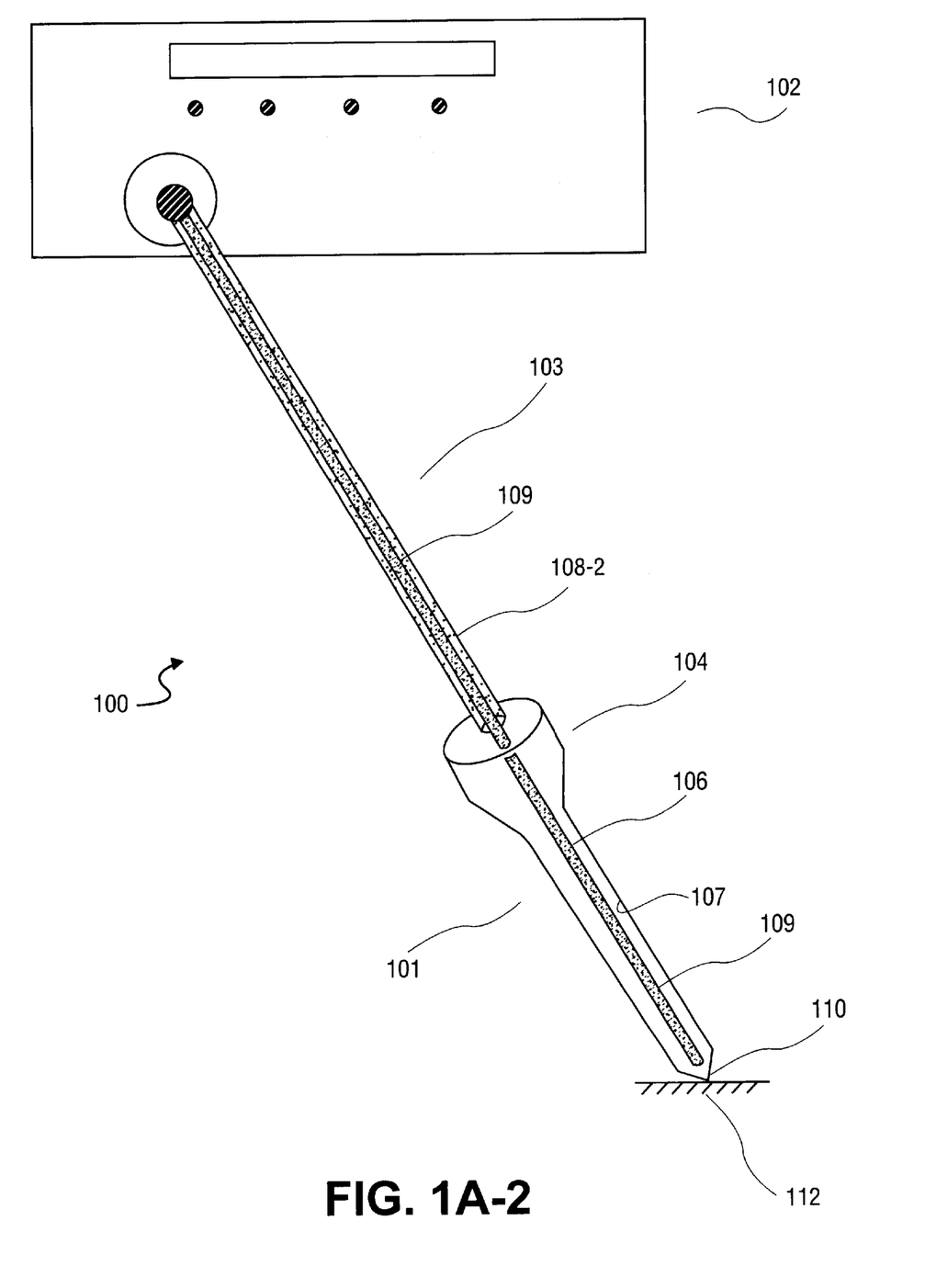

FIG. 1A-2 illustrates yet another embodiment. Here, fiber optic cable 103 includes optical fiber 109, which is surrounded by jacket 108-2. Fiber optic cable 103 may have a dimension defined by jacket 108-2, which is less than the dimension of a lumen 106 of catheter 101. Alternatively, fiber optic cable 103 may be jacketed with jacket 108-2 only along the cable portion that is not going inside catheter 103. Thus, the portion being inserted inside catheter 101 may be bare and not covered by jacket 108-2.

Figure 1B:
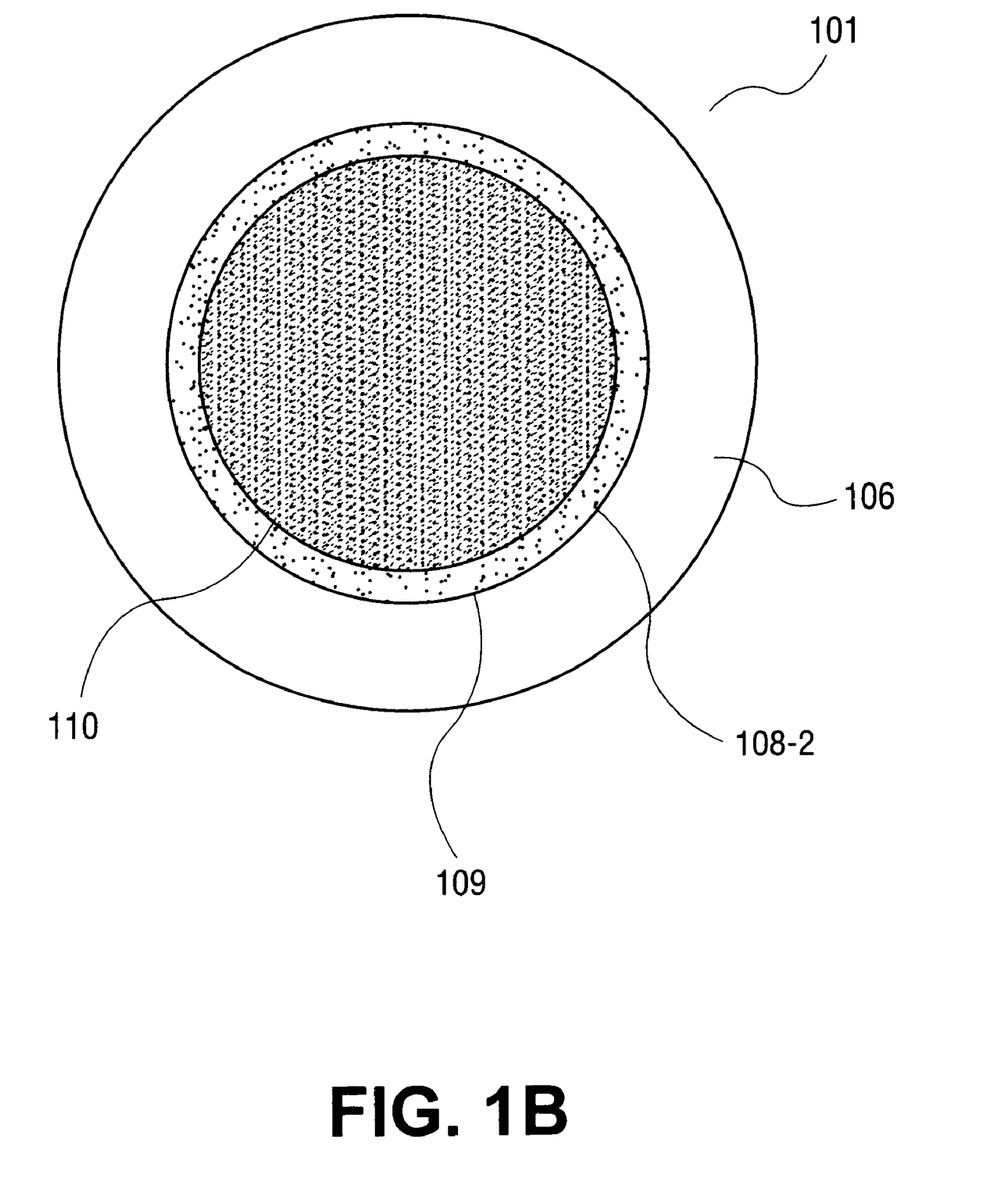
FIG. 1B illustrates a cross-section of a fiber optic cable inserted inside a catheter's lumen according to one exemplary embodiment.

In one embodiment, fiber optic cable 103 has a dimension of at least two gauge sizes smaller in diameter than the lumen 106 of the catheter 101 it is to be inserted into. FIG. 1B illustrates a cross section of this embodiment in which fiber optic cable 103 is inserted inside catheter 101.

Figure 21:
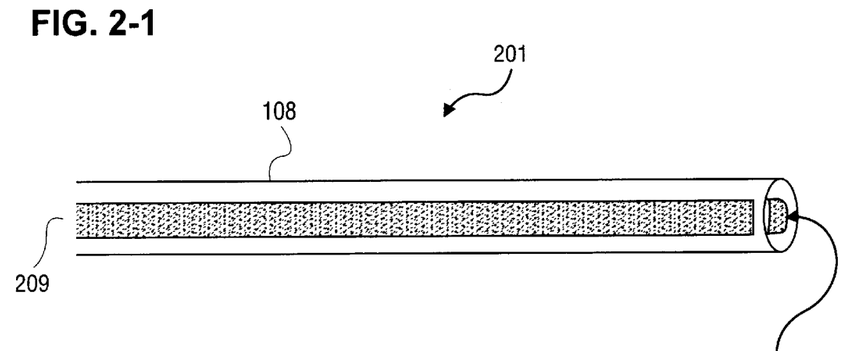
Figure 22:
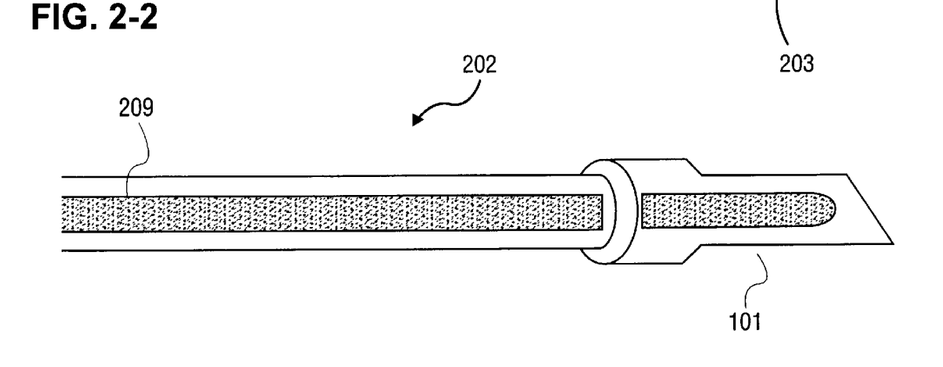
Figure 23:
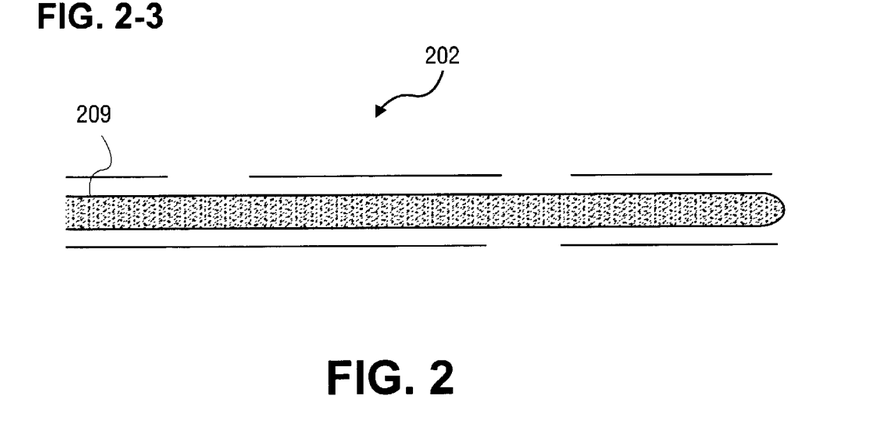

In another embodiment, fiber optic cable 103 can be polished. FIGS. 2-1, 2-2, and 2-3 illustrate differences between polished fiber optic cable 202 and nonpolished fiber optic cable 201. Polishing of a fiber optic cable typically occurs at the UV radiation emitting end of the fiber optic cable. On occasion, polishing can also occur at sections along the fiber optic cable as illustrated in FIG. 2-3. Tis polishing enables UV radiation to emit outward for a predefined length to effectively sterilize a catheter's interior as well possibly as an area surrounding the catheter.

Polishing a fiber optic cable is a common practice in the field to increase the efficiency of UV radiation emission when UV radiation emission beyond the tip of a fiber optic cable is necessary. A polished tip fiber optic cable is commercially available and can be ordered from suppliers, for example, from Fiberguide Industries, 908-647-8464.

In one embodiment when catheter 101 is small, such that the whole fiber optic cable 103 would be too large to be inserted into catheter 101, polished fiber optic cable 202 with a longer optical fiber 209, bare and void of any jacket, can be used. In that embodiment, the only section of fiber optic cable 103 that is inserted into catheter 101 is a bare section optical fiber 209 as illustrated in FIG. 2-2. Alternatively, the fiber optic cable described in FIG. 1A-1 can also be used. In such case, as illustrated in FIG. 1A-1 optical fiber 109 which is surrounded only by thin wall 108-1 and not jacket 108-2 will have a dimension that is smaller than lumen 106 of catheter 101. Thus, the whole fiber optic cable 103 will fit inside catheter 101.

Figure 3:
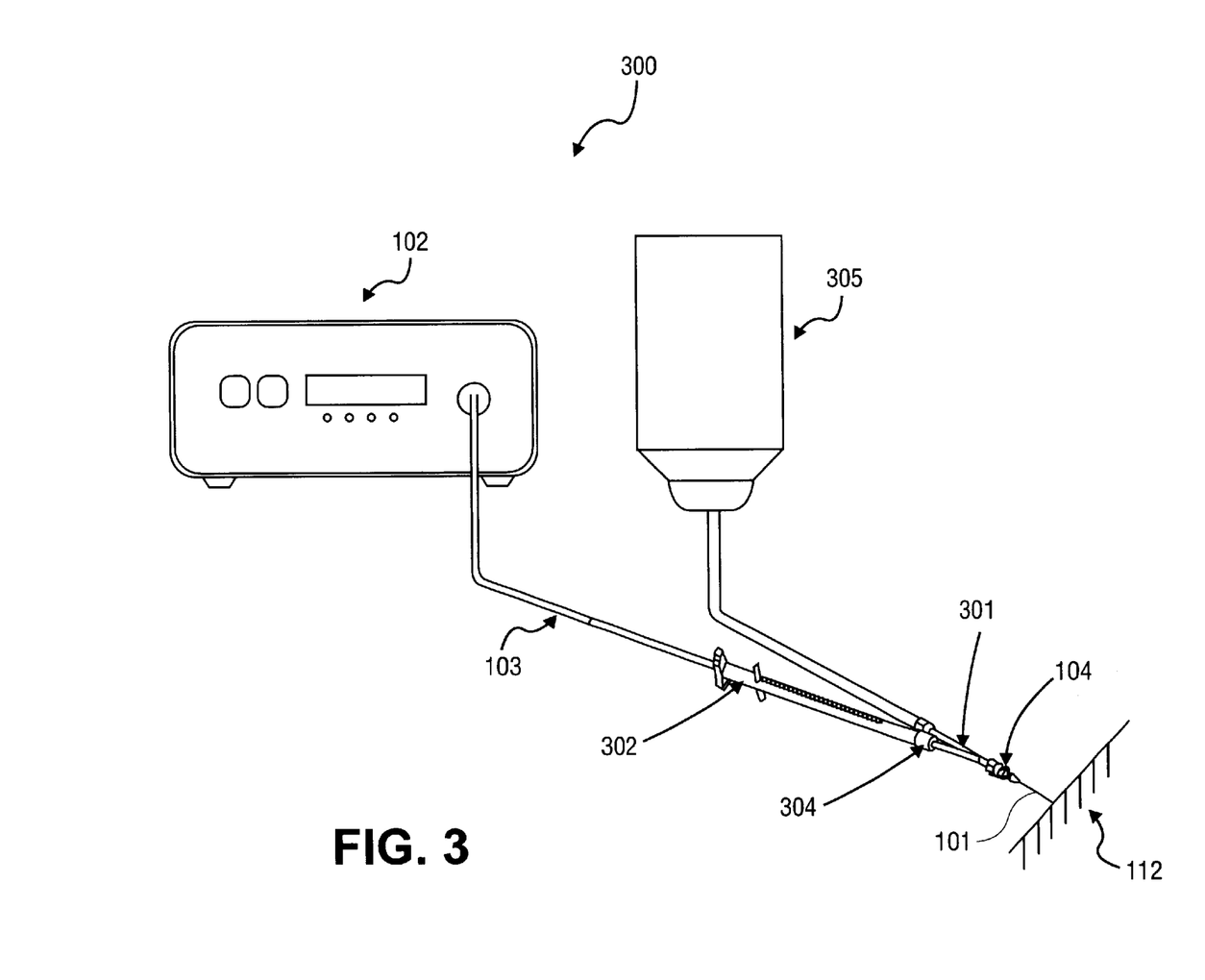
FIG. 3 illustrates a preferred embodiment of an ultraviolet radiation catheter sterilization system.
Figure 3A:
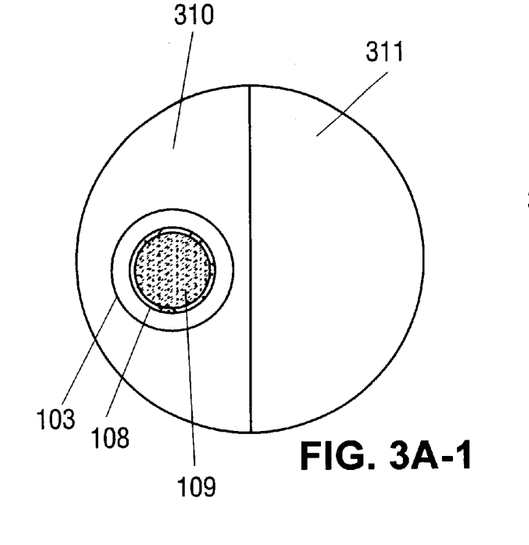
Figure 3A:
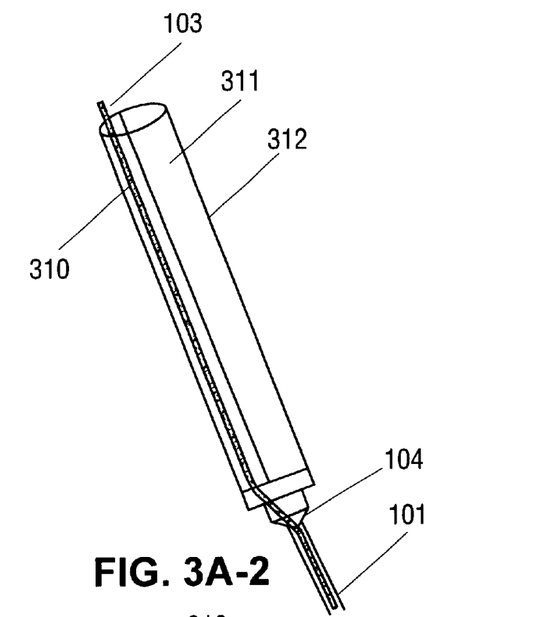
Figures 3A, 3A:
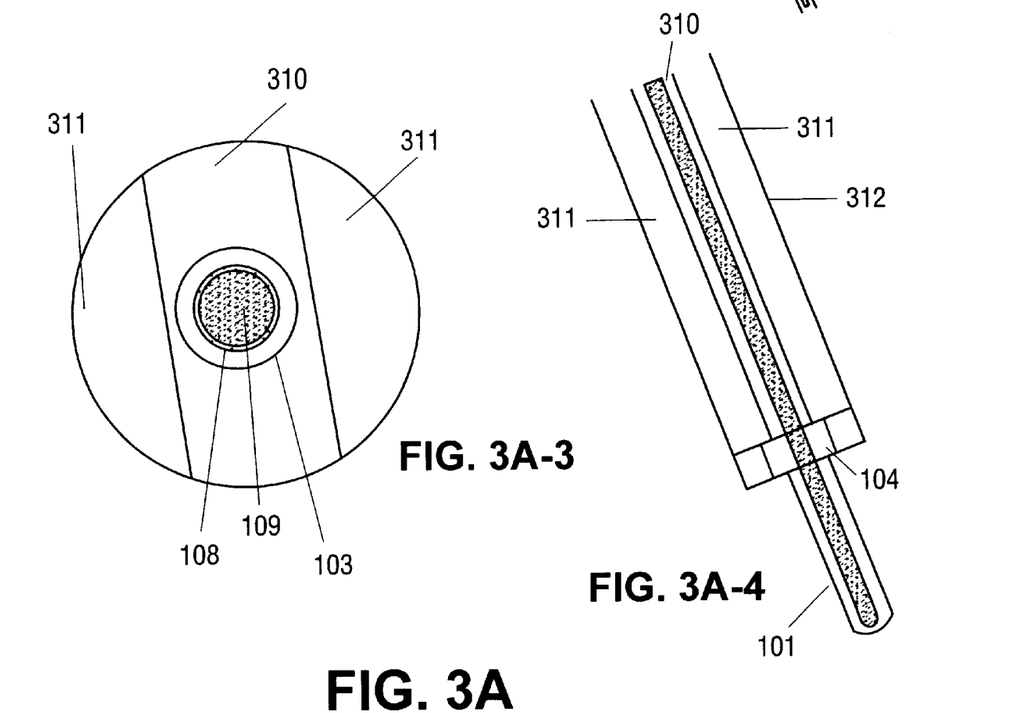

FIG. 3 illustrates another embodiment. Here, catheter sterilization assembly 300 comprises insertion tube 301, which comprises two separate paths, one for the necessary fluid source to be injected into or extracted from a patient and one for fiber optic cable 103, (more details to be shown in FIGS. 3A and 3B). Insertion tube 301 can be made out of a polycarbonate plastic material employing a standard injection molding or extrusion process well known in the art.

In one embodiment, insertion tube 301 provides guidance as well as protection for fiber optic cable 103 as it is being inserted into catheter 101. Most importantly, as illustrated in FIGS. 3A-1–4, one advantage of this embodiment is that fiber optic cable 103 can be independently inserted in cable path 310. Since cable path 310 is a separate path from fluid source path 311, contamination, interference or leakage is minimized.

FIGS. 3A-1–4 also show examples of how two-path insertion tube 312 can be designed so that fiber optic cable 103 can be independently introduced into a separate path, cable path 310, as opposed to being introduced directly into the fluid path 311. In FIG. 3A-2 separate cable path 310 can be in the center of the fluid path 311.

Figure 3B:
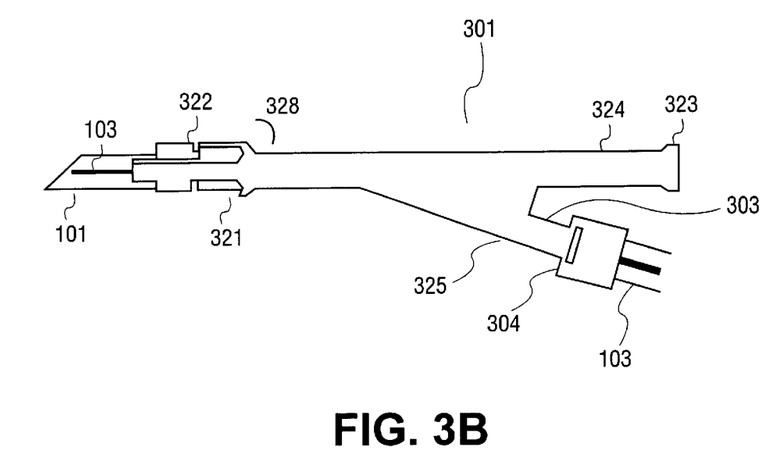
FIG. 3B illustrates an example of a Y shaped insertion tube which is a form of a two-path insertion tube.

FIG. 3B shows that "Y" shaped tube 301 is the most desirable shape according to this two-path insertion tube embodiment since it provides a convenient and minimal resistant path for the insertion of fiber optic cable 103 into catheter 101. While the Y shape is most desirable, other configurations are possible, as illustrated in FIG. 3A.

In one embodiment, as illustrated in FIG. 3, Y shaped insertion tube 301 establishes an in-line connection between fluid line 305 and catheter 101. An I.V. drip can be connected to fluid line 305. One advantage of this embodiment is that UV radiation source can be independently introduced and removed from catheter sterilization assembly 300 without affecting the I.V. drip. According to this embodiment, when Y shaped tube 301 is included in catheter sterilization assembly 300, fluid source 305 will enter catheter 101 from one leg and fiber optic cable 103 will enter a catheter from another leg (more details discussed bellow). Both the fluid source 305 and the fiber optic cable 103 will then enter catheter 101. This Y shape embodiment thus enables independent, simultaneous and smooth introduction of both fluid and fiber optic cable 103 into catheter 101. Further, Y shaped insertion tube 301 will allow fiber optic cable 103 to be inserted into catheter 101 while a fluid source is still flowing with no interference or leakage.

One advantage of an embodiment having Y shaped insertion tube 301 is that since tube 301 is connected inline with the hub and a fluid source, there is no modification necessary to an existing equipment already in use. On the other hand, when a fluid source is a substance that may be affected by the presence of UV radiation, fiber optic cable 103 can either be removed or shut off without affecting the fluid substance.

Another advantage of this embodiment is that the sterilization could possibly occur at intervals allowing the patient freedom from portable devices. Further, since a fiber optic cable is inserted or removed from its own path, no blood or body fluid goes up the catheter as the cable is being withdrawn from a patient's body when fluid pressure is greater than the blood flow.

FIG. 3B illustrates in details that Y shaped insertion tube 301 discussed above further comprises three legs, first leg 324, second leg 325, and third leg 328, each equipped with a security attachment. In one embodiment, first leg 324 connects to an I.V. drip via security attachment 323, for example, luer connection, lock or vale. Second leg 325 comprises cable insertion section 303 and connects to fiber optic cable 103 also via another security attachment, attachment 304, which can also be a luer connection, lock or valve. The remaining leg, third leg 328, attaches to catheter 101 via a standard catheter hub connection 321 as its security attachment. In one embodiment, catheter hub connection 321 can also be equipped with steel lumen 322 to provide an extra protection for the optical fiber cable 103 as illustrated also in FIG. 3B.

In another embodiment, cable insertion section 303 has a inner diameter dimension defined by the circumference of a section of fiber optic cable 103 that is to be inserted into a catheter 101. In this embodiment, cable insertion section 303 is only sized large enough for that section of the fiber optic cable 103 to be snugly inserted through.

Figure 3C:
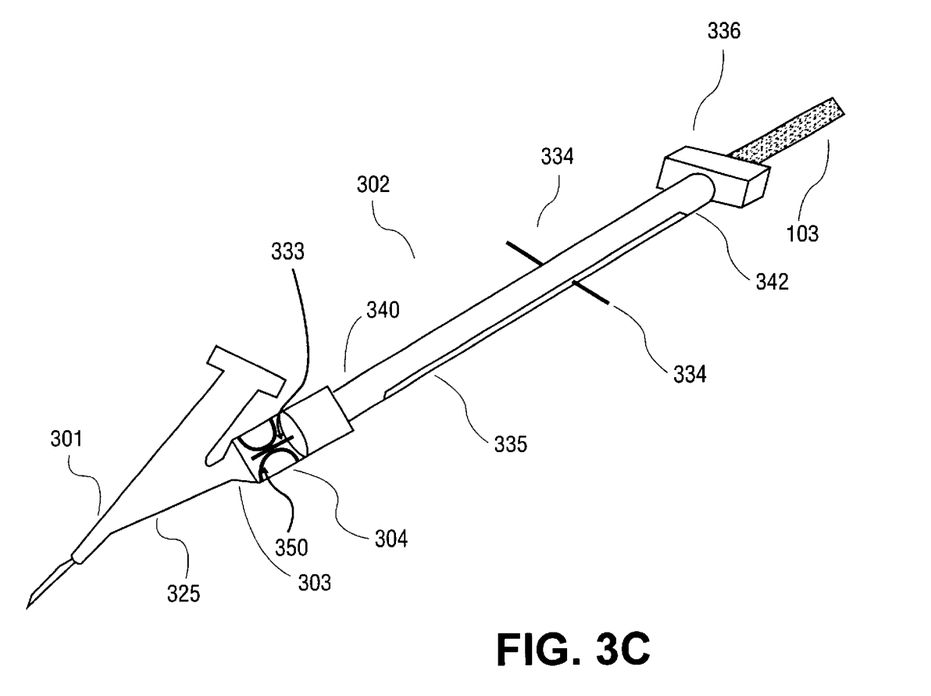
FIG. 3C illustrates a cable insertion device according to one exemplary embodiment.

In another embodiment, Y shaped insertion tube 301 is equipped with valve 350 (FIG. 3C). Valve 350 prevents fluid from going up into the cable path due to back pressure. Another advantage for this embodiment is that valve 350 prevents air from going in into catheter 101 much like putting a syringe through a rubber stopper.

In another embodiment, catheter sterilization assembly 300 further comprises cable insertion device 302 as shown in FIG. 3. FIG. 3C illustrates that cable insertion device 302 includes two ends, first end 340, and second end 342. Cable insertion device 302 can be made out of hard plastic such as polycarbonate or stainless steel. FIG. 3C also illustrates in details that first end 340 of a cable insertion device 302 can be attached to cable insertion section 303 of Y shaped insertion tube 301 on leg 325 via security attachment 304. For example, first end 340 of a cable insertion device 302 can be threaded or screwed onto leg 325 of Y shaped insertion tube 301. Second end 342 of cable insertion device 302 can be configured with nose end 336. It is through nose end 336 that fiber optic cable 103 can be inserted into cable insertion device 302.

In yet another embodiment, cable insertion device shown 302 in FIG. 3 and as detailed in FIG. 3C can also be equipped with steel lumen 333 at a first end 340. Steel lumen 333 would break a rubber seal (not shown) on attachment 304 of Y shaped insertion tube 301 as the cable insertion device 302 is being screwed onto leg 325 of Y shaped insertion tube 301. Steel lumen 333 would then penetrate valve 350.

One purpose of this rubber seal feature is to protect Y shaped insertion tube 301 from contamination especially when UV radiation sterilization process is not ongoing or necessary. Another purpose is that the seal would be airtight and thus preventing fluid from leaking. Further, any air and fluid that may leak through the valve during insertion would flow up to the valve but not beyond.

FIG. 3C also illustrates another embodiment in which, cable insertion device 302 further comprises two push rods 334 composed out of stainless steel or hard plastic. In this embodiment, cable insertion device 302 has a through slit 335 running axially along its body with an opening on each side of cable insertion device 302. Push rods 334 are essentially screws having grinding teeth (not shown). Push rods 334 are placed on through slit 335, one rod on each side of through slit 335.

One purpose of push rods 334 is to assist an operator in the insertion of fiber optic cable 103 into catheter 101. For instance, an operator would use push rods 334 to create a contact with fiber optic cable 103 that is already inserted inside the cable insertion device 302 by screwing push rods 334 through slit 335 and onto fiber optic cable 103. Push rods 334 are then pushed forward along slit 335 and fiber optic cable 103 is thus pushed forward through Y shape insertion tube 301 and into catheter 101.

Figure 4:
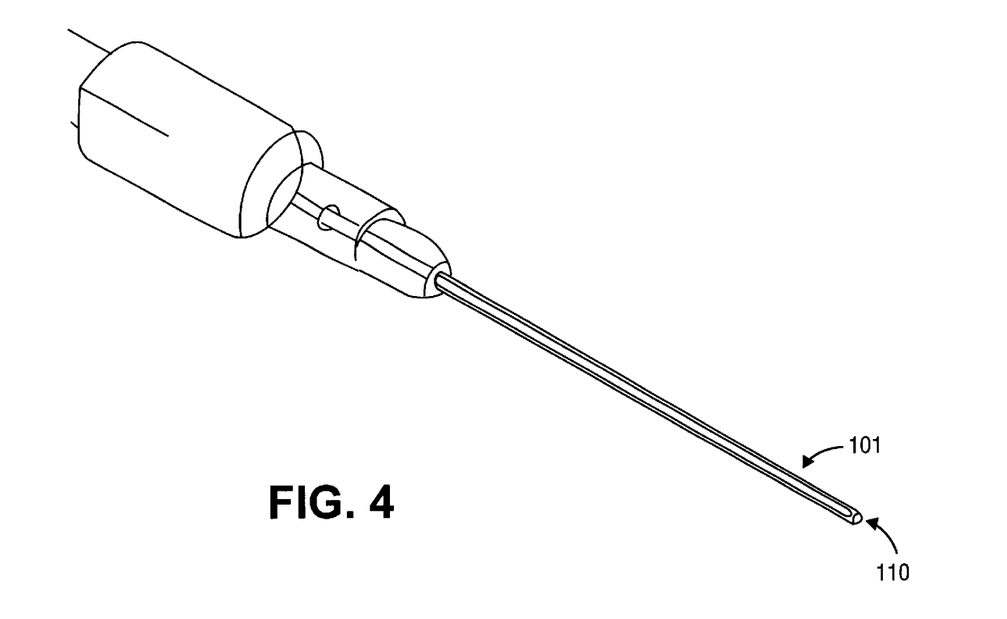
FIG. 4 illustrates a way of introducing ultraviolet radiation into a fiber optic cable.

Returning now to FIG. 3, which illustrates one exemplary method employed to effectively sterilize catheter 101 and its point of entry 112. An operator would insert catheter 101 described above into a patient's body, shown as point of entry 112. Fiber optic cable 103 is then disposed within the lumen 106 of catheter 101 (not shown in details). Following that, the operator would activate UV radiation source 102 exposing catheter tip 110 to UV radiation. FIG. 4 further demonstrates a method of using the fiber optic cable to transmit UV radiation into catheter 101. Generally, a UV radiation source would be connected to a fiber optic cable for a pre-determined amount of time, interval and duration which is sufficient to effectively sterilize the catheter.

Effective sterilization utilizing UV radiation means that UV radiation is introduced sufficiently long enough to incapacitate harmful bacteria or miicroorganism, inhibit growth of the same, reduce fungal sepsis, prevent bacteria colonization around the area of catheter entry, and maintain a sterile catheter. Sterilization thus would prevent clinical problems typically observed with infection due to short-term or long-term catheter usage. It is anticipated that clinical trials will determine the exact amount of UV radiation power and duration necessary for certain application. Different microorganism or bacteria may require variation of power levels as well as duration of the UV radiation. An example of an optimized wavelength range according to the embodiments of present invention is 200–280 nm Yet, another example of a wavelength sufficient to sterilize a catheter 101 is 254 nm The duration will be more accurately determined from experimentation, but since the area is small, the duration would be about 1 to 20 seconds or less.

Another method according to the present invention to effectively sterilize catheter 101 or its point of entry 112 is when Y shaped insertion tube 301 described above (FIG. 3) is incorporated into the system According to this method, catheter 101 may first be inserted into a patient's body, Y shaped tube 301 may then be attached to a fluid source, for example an I.V. drip, and then connected to hub 104, which may then be attached to catheter 101. At a specified time during a catheter use, either immediately for permanent insertion or at intervals for periodic use, fiber optic cable 103 is inserted into Y shaped tube 301 and through catheter 101. UV radiation source 102 may then be connected to fiber optic cable 103 and allowed to transmit UV radiation through fiber optic cable 103 to sterilize catheter 101.

In another method, cable insertion device 302 described above (FIG. 3C) is screwed onto Y shaped tube 301 at cable insertion section 303 on leg 325. While being screwed on, cable insertion device 302 equipped with steel lumen 333 will break a rubber seal (not shown) on leg 325 of Y shaped tube 301. Fiber optic cable 103 is then inserted into the cable insertion device 302 through nose end 336 on the cable insertion device 302. Then, fiber optic cable 103 is pushed down as far as it can go threading itself into Y shaped insertion tube 301 and into catheter 101. UV radiation source can then be transmitted through fiber optic cable 103 to sterilize catheter 101.

Figure 51:
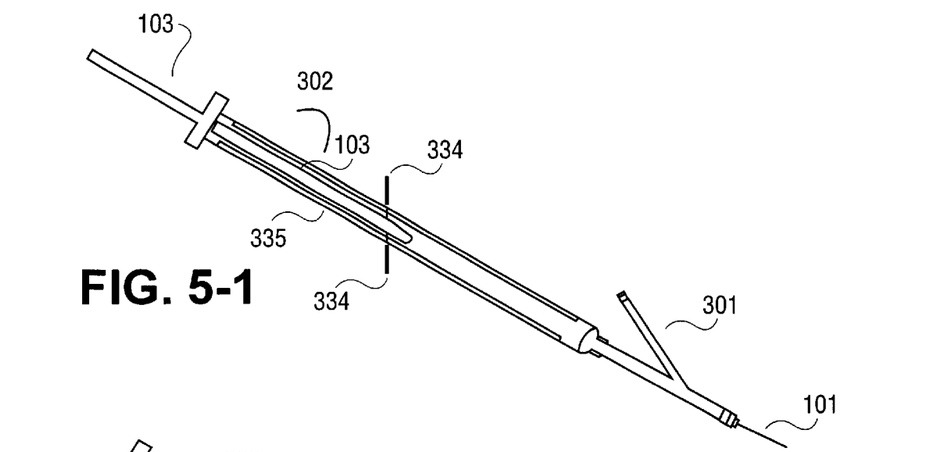
Figure 52:
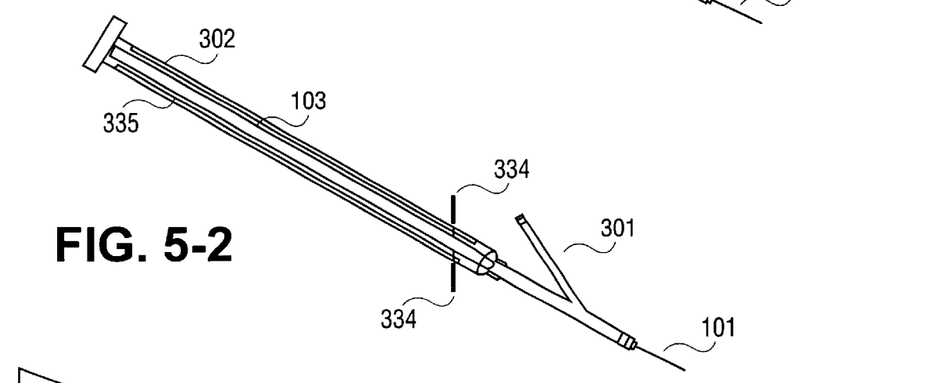
Figure 53:
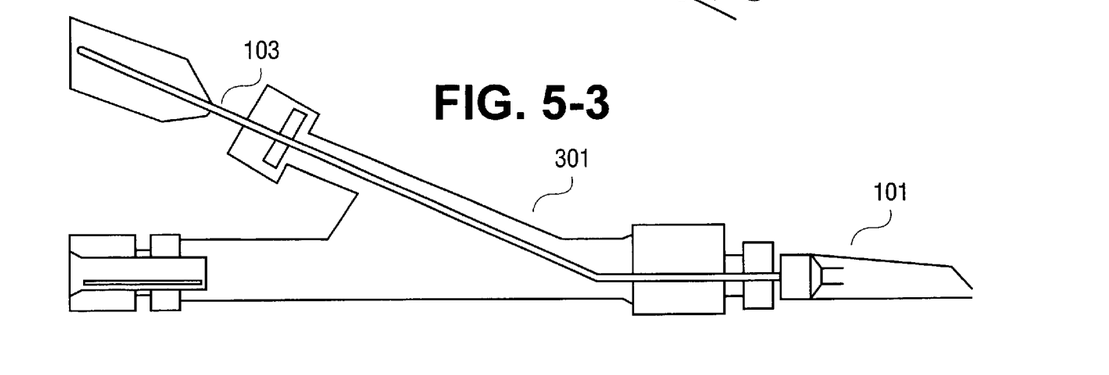

FIGS. 5-1–3 show yet another method to sterilize a catheter when two push rods 334 described above are incorporated into the sterilization assembly. In that event, the operator will insert fiber optic cable 103 into cable insertion device 302 having through slit 335 described above. The operator then will connect fiber optic cable 103 to push rods 334 by screwing down push rods 334 to create a good contact with cable 103. Following that, with fiber optic cable 103 held in place by push rods 334, the operator will slide push rods 334 forward along through slit 335 thereby forcing fiber optic cable 103 through Y shaped insertion tube 301 and into catheter 101. UV radiation source can then be conveyed into fiber optic cable 103, which will then expose catheter 101 to UV radiation.

Figure 6:
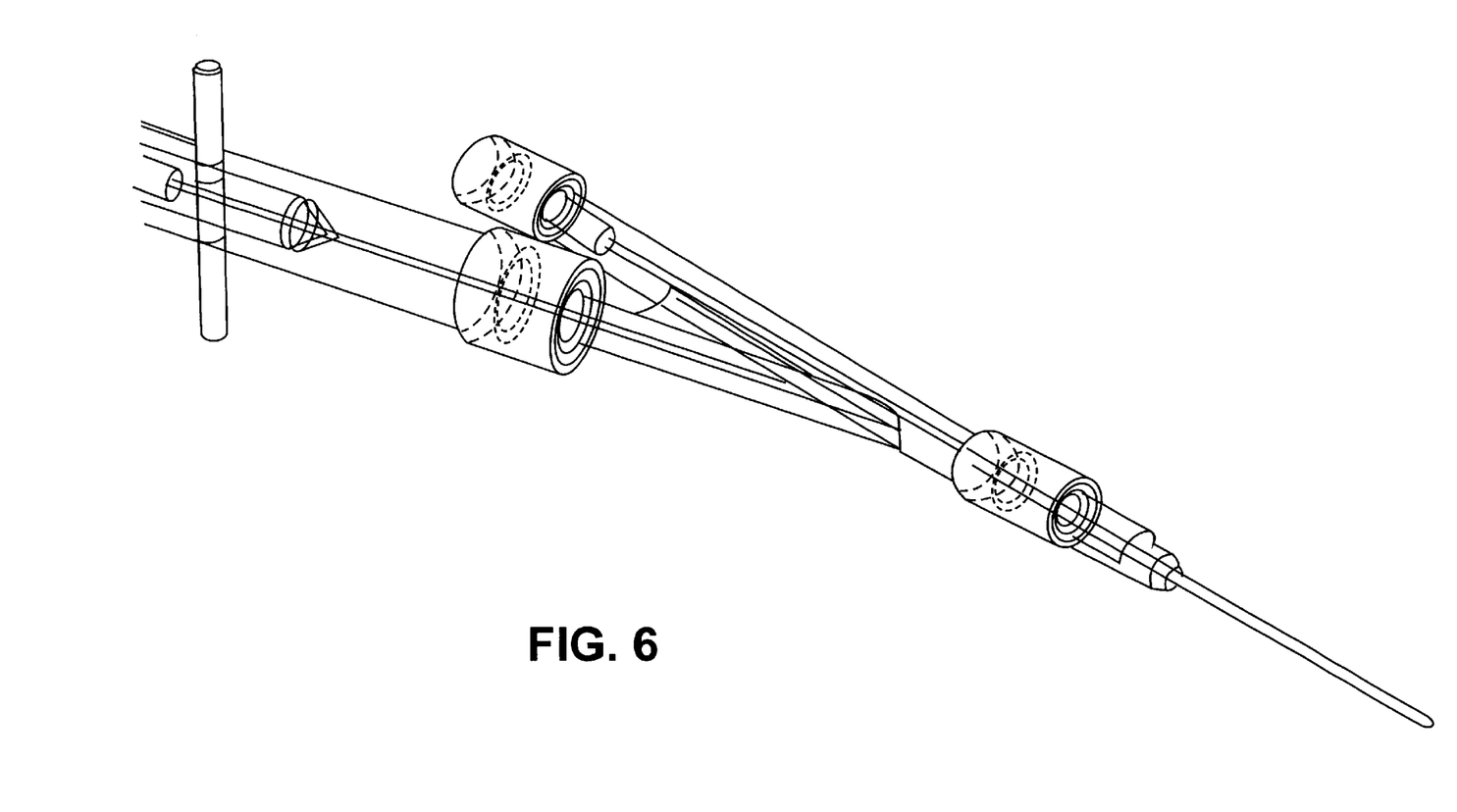
FIG. 6 illustrates a wire frame view of the ultraviolet radiation catheter sterilization system

FIG. 6 further illustrates a wire frame view of fiber optic cable 103 being inserted into catheter 101 through the use of cable insertion device and Y shaped insertion tube according to some exemplary methods of this invention.

Figure 7:
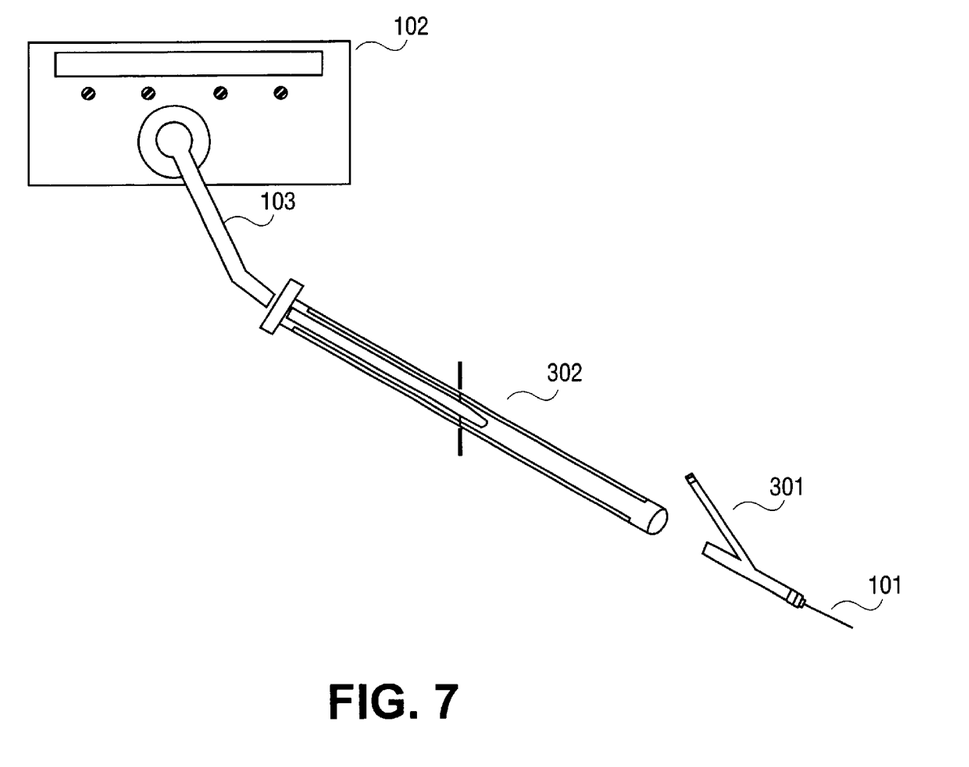
FIG. 7 illustrates an example of a method when a fiber optic cable 103 is removed from a Y shaped insertion tube.

FIG. 7 illustrates another method of catheter sterilization when fiber optic cable 103 as well as cable insertion device 302 are both removed from Y shaped insertion tube 301 which remains connected to catheter 101. Here, after fiber optic cable 103 is successfully inserted into catheter 101 through cable insertion device 302 and Y shaped insertion tube 301 as described above, UV radiation source 102 is then activated thereby transmitting UV radiation into catheter 101. After effective UV sterilization is complete, fiber optic cable 103 is pulled up by sliding push rods 334 backward, and optionally, removed from cable insertion device 302. And, cable insertion device 302 is unscrewed detaching itself from Y shaped insertion tube 301. Y shaped insertion tube 301 can then be resealed with a new rubber seal (not shown) allowing catheter 101 to remain in the patient's body and be sterilized again when necessary. Alternatively, the rubber seal can be designed so that it does not need replacing.

In another method, when an area needed to be sterilized is outside catheter 101, catheter 101 can be made out of a UV transparent plastic. In that event, the UV radiation will reach further than catheter tip 110, for example, being able to transmit through catheter wall 107 to the surrounding environment.

In the foregoing specification, the invention has been described with reference to specific exemplary embodiments and methods. It will be evident that various modifications may be made to the present invention without departing from the broader spirit and scope of the invention as set forth and in the following claims. The specification and drawings are to be regarded as illustration rather than any restriction or limitation.

It is therefore desirable, according to certain embodiment of the invention, to have a sterilization device that will go through the catheter's lumen that can easily be inserted and removed from the catheter as on a per need basis. It is also desirable, according to certain embodiment of the invention, to have a catheter sterilization device that will be simple to use and easily to adaptable to an existing catheter assembly without much modification to the existing assembly.

From the above description, it can be seen that it is desirable, according to certain embodiment of the invention, to provide apparatuses and methods for sterilizing a catheter in which no modification to the catheter is required and which can be removed from the catheter when necessary. Also, it is desirable, according to certain embodiment of the invention, to provide sterilization apparatuses and methods that would include separate paths for the fluid and a fiber optic cable to minimize contamination.

I claim:

1. A catheter assembly comprising:
   a UV radiation source;
   a catheter having a lumen which is surrounded by a first wall of said catheter;
   a fiber optic cable coupled to said UV radiation source and freely disposed within said lumen, said fiber optic cable having a second wall which surrounds a length of said fiber optic cable, said second wall having a dimension which is less than a dimension of said lumen, said fiber optic cable emitting UV radiation through at least a portion of said second wall; and
   a cable insertion device capable of coupling to said catheter, said cable insertion device having at least one slit along a portion of an outer wall.

2. A catheter assembly as in claim 1, further comprising:
   an insertion tube having a an attachment capable of connecting to said catheter, said insertion tube to guide said fiber optic cable into said catheter.

3. A catheter assembly as in claim 1, further comprising:
   an insertion tube having two separate paths, a first path for fluid source, a second path for said fiber optic cable, said two separate paths meeting at one end, said end having an attachment capable of connecting said insertion tube to said catheter, and said insertion tube to guide said fiber optic cable into said catheter.

4. A catheter assembly as in claim 1, further comprising:
   a Y shaped insertion tube comprising a first leg to connect to a fluid source using a first attachment, a second leg to connect to said fiber optic cable using a second attachment, and a third leg to connect to said catheter using a third attachment.

5. A catheter assembly as in claim 4, wherein the cable insertion device further having a first end and a second end, said first end having a nose end capable of allowing said fiber optic cable to be inserted through and said second end attaching to said second leg of said Y shaped insertion tube to guide said fiber optic cable into said catheter.

6. A catheter assembly as in claim 5, wherein said slit is a through slit having a first side and a second side, and said cable insertion device further comprises:
   a first push rod located on said first side of said through slit; and
   a second push rod located on said second side of said through slit, said first push rod and said second push rod capable of connecting to said fiber optic cable to secure said fiber optic cable within said cable insertion device.

7. A catheter assembly as in claim 1, wherein said fiber optic cable is at least two gauge sizes smaller in diameter than said catheter.

8. A catheter assembly as in claim 1, wherein said fiber optic cable is polished allowing said UV radiation source to emit outward for a predefined length along said second wall to effectively sterilize an area of interest.

9. A catheter assembly as in claim 1, wherein said fiber optic cable further comprises:
   a first end and a second end, said first end having a first fixture capable of connecting into said UV radiation source, and said second end having a second fixture which is polished to allow said UV radiation source to emit outwards for a predefined length along said second wall to effectively sterilize an area of interest.

10. A method for effectively sterilizing a catheter comprising:
    inserting a catheter having a lumen which is surrounded by a first wall of said catheter into a patient's body;
    disposing a fiber optic cable freely within said lumen, said fiber optic cable having a second wall which surrounds a length of said fiber optic cable, said second wall having a dimension which is less than a dimension of said lumen and emitting UV radiation through at least a portion of said second wall; connecting a cable insertion device to said fiber optic cable, said cable insertion device having an outer wall and at least one slit in a portion of said outer wall; and transmitting a UV radiation source into said fiber optic cable for a sufficient amount of time and duration to effectively sterilize an area of interest.

11. A method as in claim 10, further comprising:
connecting an insertion tube to said catheter using an attachment, said insertion tube guiding said fiber optic cable into said catheter.

12. A method as in claim 10, wherein said transmitting of said UV radiation source is not done simultaneously with injecting of a fluid source that interferes with said UV radiation.

13. A method as in claim 10, further comprising:
connecting an insertion tube having a first path and a second path;
dedicating said first path to a fluid source;
dedicating said second path for said fiber optic cable; and
uniting said first path and said second path at one end, said one end having an attachment capable of connecting said insertion tube to said catheter.

14. A method as in claim 10, further comprising:
providing a Y shaped insertion tube having a first leg, a second leg and a third leg;
connecting said first leg of said Y shaped insertion tube to a fluid source using a first attachment;
connecting said second leg of said Y shaped insertion tube to said fiber optic cable using a second attachment; and
connecting said third leg of said Y shaped insertion tube to said catheter using a third attachment.

15. A method as in claim 14, further comprising:
turning off said UV radiation source upon completion of sterilization; and
removing said fiber optic cable from said insertion tube.

16. A method as in claim 14, wherein said connecting said cable insertion device includes said cable insertion device further having a first end and a second end, said first end having a nose end capable of allowing said fiber optic cable to be inserted through and said second end attaching to said second leg of said Y shaped insertion tube using a fourth attachment.

17. A method as in claim 16, further comprising:
designing said cable insertion device wherein said slit is a through slit extending from a first side through to a second side of said cable insertion device;
attaching a first push rod to said first side;
attaching a second push rod to said second side;
designing said first push rod and said second push rod with grinding teeth enabling said first push rod and said second push rod to be screwed down through said through slit making a contact with said fiber optic cable inserted within said cable insertion device; and
sliding said first push rod and said second push rod forward along said through slit inserting said fiber optic cable into said second leg of said Y shaped insertion tube and into said catheter.

18. A method as in claim 17, further comprising;
sealing said Y shaped insertion tube with a rubber valve seal;
affixing a steel lumen to said cable insertion device enabling said cable insertion device to break said rubber valve seal when connecting to said second leg of said Y shaped insertion tube.

19. A method as in claim 10, wherein said disposing of said fiber optic cable is of a fiber optic cable having a dimension of at least two gauges smaller in external diameter than an internal diameter of said lumen of said catheter.

20. A method as in claim 10, further comprising:
scoring said fiber optic cable along a section which emits said UV radiation enabling said UV radiation source to emit outward for a predefined length along said wall to effectively sterilize an area of interest.

* * * * *